United States Patent [19]

Ghosh et al.

[11] 4,358,595

[45] Nov. 9, 1982

[54] 4-CHLORO-7-SULPHOBENZOFURAZAN AND SALTS THEREOF; NEW FLUORIGENIC THIOL SPECIFIC REAGENTS

[75] Inventors: Peter Ghosh, Sydney; Bela Ternai, Victoria; M. W. Whitehouse, Adelaide, all of Australia

[73] Assignee: Pierce Chemical Company, Rockford, Ill.

[21] Appl. No.: 311,078

[22] Filed: Oct. 13, 1981

[51] Int. Cl.$^3$ ............................................. C07D 271/08
[52] U.S. Cl. .................................................... 548/126
[58] Field of Search ........................................ 548/126

[56] References Cited

U.S. PATENT DOCUMENTS

| | | | |
|---|---|---|---|
| 3,501,285 | 3/1970 | Baldwin | 548/126 |
| 3,524,861 | 8/1970 | Hackmann et al. | 548/126 |
| 4,145,360 | 3/1979 | Crosby et al. | 548/126 |

Primary Examiner—Mary C. Lee

[57] ABSTRACT

New fluorigenic thiol specific reagents, 4-chloro-7-sulphobenzofurazan and salts thereof, are disclosed. The reagents are prepared by sulphonation of 4-chlorobenzofurazan. Ammonium 4-chloro-7-sulphobenzofurazan is used to label glutathione as a model thiol peptide and bovine serum albumin and jackbean urease as thiol containing proteins.

5 Claims, No Drawings

4-CHLORO-7-SULPHOBENZOFURAZAN AND SALTS THEREOF; NEW FLUORIGENIC THIOL SPECIFIC REAGENTS

The present invention relates to the labelling of biological molecules with fluorescent probes and, more particularly, to an improved probe for labelling thiol groups.

The investigation of structure, conformation and reactivity of specific sites within proteins and other biological molecules is of major importance to biochemists. The well established role of thiol groups in the control and function of many biological processes has, over the years, led to many reagents reported to be useful in studying this moiety. Covalent labelling of thiol groups by spectroscopic reagents, or probes, is a well established technique which has been employed for such investigations.

One such reagent is 4-chloro-7-nitrobenzofurazan (Nbf-Cl), described in Ghosh, P. B. and Whitehouse, M. W., (1968), Biochem J., 108; 155, but is possesses several disadvantages. Nbf-Cl has low aqueous solubility, is believed to be cytotoxic and mutagenic, and like many covalent probes, shows a lack of specificity for any one functional group type. In addition, Nbf derivatives may be substituted at more than one position under non-biological conditions due to the high activity of the benzofurazan ring. There are also reports indicating that the expected Nbf-4-thio derivative is not the only product formed on reaction of this reagent with proteins or low molecular weight thio compounds. The possible simultaneous formation of several products within proteins complicates the use of Nbf-Cl for many analytic and kinetic investigations.

In accordance with the present invention there are provided new compounds which, when used as fluorescent probes, substantially eliminate the problems described above with respect to Nbf-Cl. These new compounds are 4-chloro-7-sulphobenzofurazan-(Sbf-Cl) and its water soluble salts. The compounds have the structure

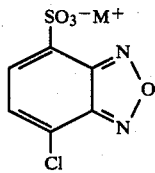

wherein $M^+$ is $H^+$, $Na^+$, $NH_4^+$ or $K^+$. The salts, particularly ammonium, are especially useful. The compounds are water soluble, highly specific for thiol groups in aqueous media, are free of cytotoxic properties, and not mutagenic.

Sbf-Cl and its salts can be prepared in three basic steps. The first step involves the oxidation of 2,6-dichloroaniline to 2,6-dichloronitrosobenzene using hydrogen peroxide (R. R. Holmes and R. P. Bayer. J. Amer. Chem. Soc., 82: 3454 (1960)). The oxidation proceeds via the hydroxylamine so at least 2 molar equivalents of hydrogen peroxide are required. The second step is synthesis of 4-chloro benzofurazan by heating 2,6-dichloronitrosobenzene with sodium azide in dimethylformamide (A. J. Boulton, P. B. Ghosh and A. R. Katritzky. Tet. Letters. 25: 2887 (1966)). The last step is sulphonation of 4-chlorobenzofurazan using, for example, oleum at 150°-160° C. The following examples illustrate preparation of compounds of this invention by the above-described steps.

I

2,6-DICHLORONITROSOBENZENE

To a solution of 2,6-dichloroaniline (42.3 g, 0.26 mole) in glacial acetic acid (520 ml) in a 1 litre conical flask at room temperature, was added 100 vol hydrogen peroxide (157 ml, 1.38 mole). The flask was plugged with absorbant cotton, and set aside on a thermostatically controlled water bath at a temperature of 25°-30° C. for 70 hours. The flask was then cooled to 5° C., and the crystalline solid collected on a sintered glass funnel, washed with ethanol-pet. ether (40°-60°) (200 ml, 1:1, v/v), and dried in an oven at 90° C. The buff leaflets weighed 40.25 g (87.6%) m.p. 171°-172° C.

II

4-CHLOROBENZAFUROZAN

A mixture of 2,6-dichloronitrosobenzene (40 g, 0.24 mole) in N,N-dimethylformamide (250 ml) was placed, under a hood, in a 500 ml three-necked flask fitted with a stirrer, dropping-funnel, and 250° C. thermometer. The stirrer was started and the flask was heated to 95° C. with a heating mantle whereupon the nitroso compound completely dissolved and the solution assumed a deep-green color. The mantle was then switched off, and a solution of sodium axide (16 g, 0.25 mole) in aq. dimethyl sulphoxide (100 ml, 1:4, v/v) was added dropwise over a period of 20 min. The temperature slowly rose to 115° C. and the original green solution changed to brown. After an additional 10 min. stirring, the solution was cooled to 30° C. and poured onto ice-water ($10^3$ ml). with continuous agitation. The light grey precipitate was collected, washed with ethanol-water (100 ml, 1:20, v/v) and then pressed down well. The crude solid was then transferred to a 500 ml round-bottom flask and steam distilled with the receiver placed in an ice bath. During the steam distillation, the water passing through the condenser was occasionally turned off in order to clear the solidified product which had built up. After an hour a brown oil began to pass over and then the distillation was stopped. The material collected was then transferred to a mortar and ground with pestle to a fine paste. The product was then transferred to a vacuum-desicator, and dried over silica-gel. The white product obtained weighed 26.8 g (75%) m.p. 83°-84° C.

III

7-CHLORO-4-SULPHOBENZOFURAZAN (AMMONIUM SALT)

4-Chlorobenzofurazan (2.4 g, 16 mmole) was dissolved in oleum (7 ml) and the solution was heated at 150°-160° C. for 4 hours while protected from atmospheric moisture by a calcium chloride drying tube. The solution was then cooled and slowly poured onto ice (100 g.). The solution was then neutralized carefully with ammonium hydroxide until precipitation of the ammonium salt occurred. The precipitated salt was collected on a sintered glass funnel and recrystallized from water acetone (9:1). The product decomposes, without melting, above 330° C. Elemental analysis: calculated for $C_6H_6N_3O_4SCl$: C, 28.63; H, 2.41; N, 16.70; S, 25.43; Cl, 14.09%. Found: C, 28.40; H, 2.45; N, 16.37; S, 26.50; Cl, 13.90%.

$\lambda_{max\ (H_2O)} = 324$ nm, $\epsilon_{max\ (H_2O)} = 6.5 \times 10^3 M^{-1}$.

Neutralization of the dilute reaction mixture with sodium hydrogen carbonate instead of ammonium hydroxide, affords the sodium salt.

Use of Sbf-Cl (ammonium salt) to label reduced glutathione, GSH, is illustrated by the following example:

IV

The ammonium salt of Sbf-Cl (0.5 g, 2 mmole) and GSH (0.3 g, 1 mmole) were dissolved in 0.1 M sodium borate at pH 10 containing 10 mM EDTA, and the solution was maintained at 40° C. for 1 hour. After freeze drying, the residue was dissolved in 1% aqueous acetic acid (4 cm$^3$) and applied to a 1.9×42 cm column of Bio-Gel P-2 (200–400 mesh) and eluted with 1% acetic acid in water. The product chromatographed as a yellow fluorescent band which was collected over 25 fractions (1 cm$^3$ each). Fractions 7 to 18 were shown by TLC, not to be contaminated with GSH or Sbf-Cl, which were respectively in the leading and trailing edges of the product band. These fractions were pooled and lyophilized. The purity of the product was established by TLC on silica gel in three solvent systems: 1-propanol/water (10:3); methanol/ammonia (25:1) and 1-butanol/acetic acid/water (90:25:10) where it migrated as a single fluorescent spot (excitation at 390 nm, measured at 510 nm) which was also positive to iodine and ninhydrin stains. The melting point was not determined due to the high hygroscopicity of this compound. Elemental analysis: calculated for the decahydrate, $C_{16}H_{41}N_6O_{20}S_2$: C, 27.39; H, 5.89; N, 11.98; S, 9.14%. Found: C, 26.61; H, 5.17: N, 11.62; S, 9.00%.

$\lambda_{max\ (H2O)} = 378$ nm, $\epsilon_{max\ (H2O)} = 5.4 \times 10^3 M^{-1} cm^{-1}$ As shown in the following table bovine serum albumin and jackbean urease can be similarly labelled with Sbf-Cl, rendering them fluorescent.

As shown, enhanced labelling of both proteins can be achieved by releasing additional sulphydryl groups through reduction with dithiothreitol.

RELATIVE FLUORESCENCE OF Sbf LABELLED PROTEIN THIOLS

| Protein | Relative Fluorescence Intensity[a] | |
|---|---|---|
| | Untreated[b] | Treated[c] |
| Blank | 0 | 5 |
| Bovine Serum Albumin (3 mg/ml) | 16 | 40 |
| Jack Bean Urease (1 mg/ml) | 35 | 100 |

[a] Excitation at 390 nm, emission at 510 nm. The arbitrary units are relative to the 100 units assigned to the treated jack bean urease solution.
[b] Reactions were for 4 hours at 37° C. in 100 mM borate buffer, pH 8.0 with 1 mM EDTA and 0.2 mM Sbf—Cl (ammonium salt).
[c] Prior to labelling with ammonium salt of Sbf—Cl (0.2 mM), the proteins were treated with 0.1 mM dithiothreitol under the same buffer conditions at room temperature for 30 minutes and 0.1 mM sodium arsenite was added to bind unoxidized dithiothreitol.

We claim:
1. The compound 4-chloro-7-sulphobenzofurazan and its water soluble salts.
2. The compound having the structure

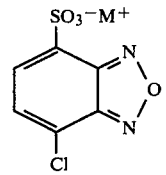

wherein M+ is H+, Na+, NH$_4$+ or K+.

3. The compound of claim 2 wherein M+ is Na+, NH$_4$+ or K+.
4. The compound of claim 3 wherein M+ is Na+.
5. The compound of claim 3 wherein M+ is NH$_4$+.

* * * * *

UNITED STATES PATENT AND TRADEMARK OFFICE
CERTIFICATE OF CORRECTION

PATENT NO. : 4,358,595
DATED : November 9, 1982
INVENTOR(S) : Peter Ghosh et al

It is certified that error appears in the above-identified patent and that said Letters Patent is hereby corrected as shown below:

On the title page assignee should read

--(73) Assignee: LaPuta Research Pty., Ltd. --.

Signed and Sealed this

Twenty-fourth Day of April 1984

[SEAL]

*Attest:*

GERALD J. MOSSINGHOFF

*Attesting Officer*  *Commissioner of Patents and Trademarks*